United States Patent [19]

Jozic

[11] 4,396,622

[45] Aug. 2, 1983

[54] CERTAIN 1-(TRIFLUOROMETHYLPHENYL SULFONAMIDOALKYL) AZACYCLOALKANES AND THEIR USE AS ANTI-ARRHYTHMIC AGENTS

[75] Inventor: Ljerka Jozic, Hanover, Fed. Rep. of Germany

[73] Assignee: Johann A. Wuelfing, Fed. Rep. of Germany

[21] Appl. No.: 348,212

[22] Filed: Feb. 12, 1982

Related U.S. Application Data

[63] Continuation of Ser. No. 148,140, May 9, 1980, abandoned.

[30] Foreign Application Priority Data

May 23, 1979 [GB] United Kingdom ................ 7917892

[51] Int. Cl.$^3$ .................... A61K 31/54; C07D 295/10; A61K 31/395

[52] U.S. Cl. ................................. 424/250; 424/248.5; 424/267; 424/274; 544/159; 544/398; 546/232; 548/569

[58] Field of Search ................ 546/232; 544/159, 398; 424/248.5, 250, 267, 274; 260/326.82; 548/569

[56] References Cited

PUBLICATIONS

Moreau et al., Eur. J. Chem. Chemica Therapeutica Sep.-Oct. 1977, vol. 12(5) pp. 421-425.
Reynaud et al., Chimica Therapeutica (1971) vol. 6(1) pp. 25-41.
Silberg et al., Chem. Abstr., vol. 55 (1961), 4802i.

*Primary Examiner*—Henry R. Jiles
*Assistant Examiner*—Bernard Dentz

*Attorney, Agent, or Firm*—Jacobs & Jacobs

[57] ABSTRACT

Pharmaceutical compositions which comprise a compound of the formula (I):

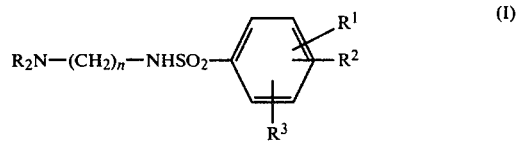

or a salt thereof wherein $NR_2$ represents a piperidyl, pyrrolidyl, morpholino or N-methyl-piperazyl group any of which may substituted by one or two methyl groups; $R^1$ represents fluorine, chlorine, bromine, iodine, lower alkoxyl, hydroxyl, acetoxyl, nitro, cyano, amino, dimethylamino, lower alkyl, trifluoromethyl, methylthio, ethylthio, methoxycarbonyl, ethoxycarbonyl, acetamido or carboxamido; $R^2$ represents hydrogen, fluorine, chlorine, bromine, iodine, lower alkoxyl, hydroxyl, lower alkyl; $R^3$ represents hydrogen, chlorine or lower alkyl; or $R^1$ and $R^2$ when on adjacent carbon atoms may together represent a polymethylene group containing from 3 to 5 carbon atoms; and n is 2, 3 or 4; and a pharmaceutically acceptable carrier, compounds of formula (I) except those wherein $R^1$ is a 2-methoxyl group, and 2,4-dimethyl-1-[2-(4-bromophenylsulphonamido)ethyl]pyrrolidine and 2,4-dimethyl-1-[2-(4-bromophenylsulphonamido)ethyl]pyrrolidine, a process for the preparation of compounds of the formula (I) and 2,4-dimethyl-1-[2-(4-bromophenylsulphonamido)ethyl]pyrrolidine and 2,4-dimethyl-1[2-(4-iodophenylsulphonamido)ethyl]pyrrolidine as antiarrhythymic agents.

8 Claims, No Drawings

CERTAIN 1-(TRIFLUOROMETHYLPHENYL SULFONAMIDOALKYL) AZACYCLOALKANES AND THEIR USE AS ANTI-ARRHYTHMIC AGENTS

CROSS-REFERENCE

This is a continuation of Ser. No. 148,140 filed May 9, 1980 and now abandoned.

Various sulphonamides are known as chemical curiosities [see for example Braun et al, Annalen, 445, 253 (1925) or Curwain et al, J. Med. Chem., 14, 737 (1971)] or as pharmaceutically active agents [see for example West German Patent Application No. 2623447, which relates to local anaesthetics, West German Patent Application No. 2710047 which relates to anti-anginal compounds, and West German Patent Application No. 2545496 which relates to platelet aggregation inhibitors].

However, none of these known sulphonamides have been reported as anti-arrhythmic agents. It is desirable to provide anti-arrhythmic agents possessing low acute toxicity. A group of such compounds has now been found.

The present invention provides a pharmaceutical composition which comprises a compound of the formula (I):

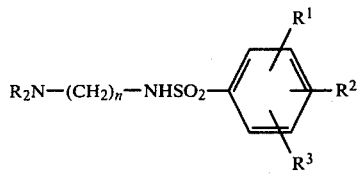

or a salt thereof wherein $NR_2$ represents a piperidyl, pyrrolidyl, morpholino or N-methyl piperazyl group, any of which may substituted by one or two methyl groups; $R^1$ represents fluorine, chlorine, bromine, iodine, lower alkoxyl, hydroxyl, acetoxyl, nitro, cyano, amino, dimethylamino, lower alkyl, trifluoromethyl, methylthio, ethylthio, methoxycarbonyl, ethoxycarbonyl, acetamido or carboxamido; $R^2$ represents hydrogen, fluorine, chlorine, bromine, iodine, lower alkoxyl, hydroxyl, lower alkyl; $R^3$ represents hydrogen, chlorine or lower alkyl; or $R^1$ and $R^2$ when on adjacent carbon atoms may together represent a polymethylene group containing from 3 to 5 carbon atoms; and n is 2, 3 or 4; and a pharmaceutically acceptable carrier.

When used herein lower alkyl means 1 to 4 carbon atoms and more suitably means 1 to 3 carbon atoms, preferably one carbon atom.

Apt values for $NR_2$ include piperidyl, 2-methylpiperidyl 2,6-dimethylpiperidyl, pyrrolidyl, 2-methylpyrrolidyl, 3-methylpyrrolidyl, 2,3-dimethylpyrrolidyl, 2,4-dimethylpyrrolidyl, 2,5-dimethylpyrrolidyl, morpholino and N-methylpiperazyl.

Favoured values for $NR_2$ include the 2,6-dimethylpiperidyl, pyrrolidyl, 2,4- and 2,5-dimethylpyrrolidyl N-methylpiperazyl and morpholino groups, more favourably the 2,4- and 2,5-dimethylpyrrolidyl groups. Preferably the dimethylpyrrolidyl groups are in the form of their cis isomers. A highly favoured value for $NR_2$ is the cis-2,5-dimethylpyrrolidyl group.

From the foregoing it will be realised that certain suitable compounds in the compositions of this invention include those of the formulae (II) to (VII).

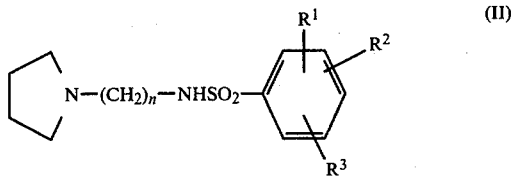

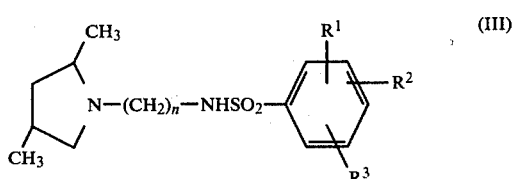

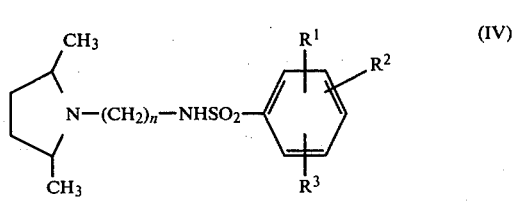

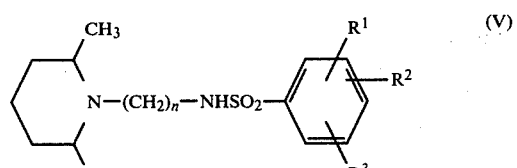

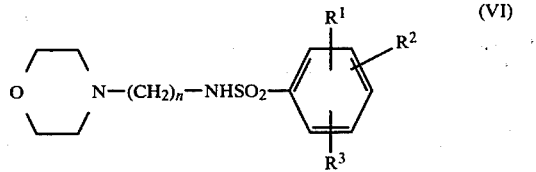

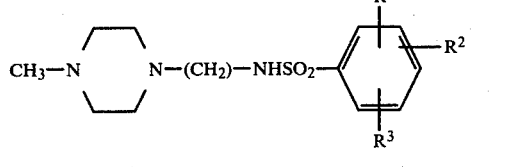

and salts thereof, wherein n, $R^1$, $R^2$ and $R^3$ are as defined in relation to formula (I).

n may be 2, 3 or 4 in formula (I).

More suitably n is 2 or 3 in respect of formula (I), but more suitably n is 2.

Certain favoured groups $R^1$ in respect of formula (I), include acetamido, amino, methyl, ethyl, isopropyl, methoxy, fluorine, chlorine, bromine, iodine, and trifluoromethyl. Preferred $R^1$ values include acetamido, amino and trifluoromethyl, in particular trifluoromethyl.

Certain favoured groups $R^2$ in respect of formula (I), include hydrogen, chlorine, methyl and iso-propyl. Preferred $R^2$ values include hydrogen.

Certain favoured groups $R^3$ in respect of formula (I), include hydrogen, chlorine and methyl and iso-propyl. Preferred $R^3$ values include hydrogen. Preferably $R^2$ and $R^3$ are the same.

With respect to formula (II) $R^1$ is favourably amino, methyl, fluorine, iodine or trifluoromethyl. Favourably $R^2$ and $R^3$ are the same and are each hydrogen or methyl.

Suitably n is 2 or 3, preferably 2.

Certain favoured compounds of the formula (II) thus include those of the formula (X):

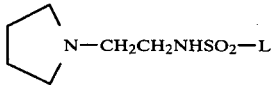

and salts thereof, wherein L is 4-aminophenyl, 4-fluorophenyl, 4-iodophenyl or 3-trifluoromethylphenyl.

Other favoured compounds include:

1-[3-(4-iodobenzenesulphonamido)propyl]pyrrolidine and
1-[3-(2,4,6-trimethylbenzenesulphonamido)propyl]pyrrolidine, and salts thereof.

With respect to formula (III) $R^1$ is favourably chlorine or trifluoromethyl preferably trifluoromethyl. Favourably $R^2$ and $R^3$ are the same and are each hydrogen or chlorine, preferably hydrogen.

When $R^1$ is chlorine, n is preferably 3, and when $R^1$ is trifluoromethyl, n is preferably 2.

Certain favoured compounds of the formula (III) thus include 2,4-dimethyl-1-[3-(2,4,5-trichlorobenzenesulphonamido)propyl]pyrrolidine and salts thereof.

Certain preferred compounds include 2,4-dimethyl-1-[2-(3'-trifluoromethylbenzenesulphonamido)ethyl]pyrrolidine, and salts thereof.

With respect to formula (IV), $R^1$ is preferably trifluoromethyl. $R^2$ and $R^3$ are preferably the same and are each hydrogen.

n is preferably 2.

Certain preferred compounds of the formula (IV) thus include 2,5-dimethyl-1-[2-(3-trifluoromethylbenzenesulphonamido)ethyl]pyrrolidine and salts thereof.

With respect to formula (V), $R^1$ is favourably trifluoromethyl. $R^2$ and $R^3$ are favourably the same and are each hydrogen.

n is preferably 2.

Certain favoured compounds of the formula (VI) thus include N-[2-(4-acetamidobenzenesulphonamido)ethyl]morpholine and salts thereof.

With respect to formula (VII) $R^1$ is favourably chlorine, Favourably $R^2$ and $R^3$ are the same and are each chlorine.

n is suitably 3.

Certain favoured compounds of the formula (VII) thus include 1-[2-(2,3,4-trichlorobenzenesulphonamido)-propyl]piperazine and salts thereof.

Compounds of the formulae (III) and (IV) and salts thereof are preferred, in particular their cis isomers.

Certain particularly preferred compounds of the formula (I) thus include those of the formulae (XI) and (XII):

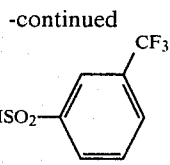

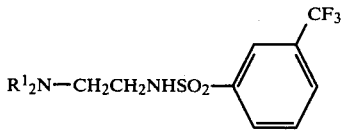

and salt thereof, wherein $R^1_2N$ is cis-2,4-dimethylpyrrolidyl and $R^2_2N$ is cis-2,5-dimethylpyrrolidyl.

It will of course be realised that when $NR_2$ in the compounds of the formula (I) is asymmetrically substituted by one methyl group, the $NR_2$ group has a chiral centre. Compounds of the formula (I) containing such $NR_2$ groups are the thus capable of existing in a number of stereoisomeric forms.

The invention extends to compositions containing any of the stereoisomeric forms including enantiomers of the compounds of the formula (I) and to mixtures thereof, including racemates. The different stereoisomeric forms may be separated one from the other by the usual methods, or any given isomer may be obtained by stereospecific or asymmetric synthesis.

The salts of the compounds of the formulae (I) to (XII) include acid addition salts and are preferably acid addition salts with pharmaceutically acceptable acids. Such acids may be inorganic or organic acids such as hydrochloric, hydrobromic, sulphuric, methanesulphonic, acetic, citric, lactic, tartaric, propionic, benzoic, fumaric and the like.

The salts of the compounds of the formulae (I), to (XII) also include pharmaceutically acceptable quaternary ammonium salts. Examples of such salts include such compounds quaternised by compounds such as $R^4-Y$ wherein $R^4$ is $C_{1-6}$ alkyl, phenyl-$C_{1-6}$ alkyl or $C_{5-7}$ cycloalkyl, and Y is an anion of an acid. Suitable examples of $R^4$ include methyl, ethyl and n- and iso-propyl; and benzyl and phenylethyl. Suitable examples of Y include the halides such as chloride, bromide and iodide.

Examples of salts also include pharmaceutically acceptable internal salts such as N-oxides.

The composition of this invention may be adapted for administration by mouth or by injection. Most suitably the composition will be in unit-dose form and such unit-doses will normally contain from 1 mg to 100 mg and more usually from 2 mg to 50 mg of the active agent.

These compositions may be administered 1 to 6 times daily or more usual 2 to 4 times daily in such manner that the daily dose for a 70 kg adult is about 1 mg to 250 mgs and more usually 50 mg to 200 mg, for example 10 mg to 75 mg. The compositions of this invention may be fabricated in conventional manner, for example they may be presented as tablets or capsules for oral administration or as dry powders sealed into ampoules for reconstitution with water or saline for injection. Tablets and capsules may contain carriers such as disintegrants, binders, lubricants, colorants and the like in conventional manner. They may therefore contain such agents as microcrystalline cellulose, lactose, starch, polyvinylpyrrolidone, sodium starch glycollate, magnesium stearate and the like. Tablets may be prepared by conventional mixing and compressing operations and capsules may be prepared by conventional mixing and filling operations.

Certain compounds of this invention are novel. This invention therefore also provides compounds of formula (I) as hereinbefore defined except those wherein R[1] is a 2-methoxyl group, and 2,4-dimethyl-1-[2-(4-bromophenylsulphonamido)ethyl]pyrrolidine and 2,4-dimethyl-1-[2-(4-iodophenylsulphonamido)ethyl]pyrrolidine.

Favoured and preferred compounds of this group include those so described under formulae (I) to (XII).

A group of compounds within the novel compounds of the formula (I) are those wherein R[2] and R[3] are not both hydrogen.

Favoured compounds of this group include 1-[3-(2,4,6-trimethylbenzenesulphonamido)propyl]pyrrolidine;
2,4-dimethyl-1-[3-(2,4,5-trichlorobenzenesulphonamido)propyl]pyrrolidine; and
4-methyl-1-[3-(2,3,4-trichlorobenzenesulphonamido)-propyl]piperazine.

The invention in its relevant aspect extends to each of the stereoisomeric forms, including enantiomers, of the compounds of the formula (I) described above and to mixtures thereof, including racemates.

The medicinal use of 2,4-dimethyl-1-[2-(4-bromophenylsulphonamido)ethyl]pyrrolidine and 2,4-dimethyl-1[2-(4-iodophenylsulphonamido)ethyl]pyrrolidine is novel. Accordingly the present invention also provides these two compounds as antiarrhythmic agents.

The invention also provides a method of treatment or prophylaxis of cardiac arrhythmia in humans, comprising administering to the sufferer a therapeutically effective amount of a compound of the formula (I)

The compounds of this invention and salts thereof may be prepared by the reaction of a compound of the formula (XIV):

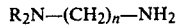

$R_2N-(CH_2)_n-NH_2$ (XIII)

wherein $R_2$ and n are as defined in relation to formula (I) and a compound of the formula (XIV):

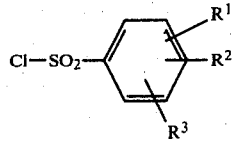

or a chemical equivalent thereof, wherein R[1], R[2] and R[3] are as defined in relation to formula (I); and optionally forming a salt of the resultant compound of the formula (I).

Chemical equivalents of the compounds of the formula (VII) include the corresponding bromide and iodide.

The preceding condensation reaction is generally effected at ambient temperature and normal pressure in a convenient solvent such as benzene or toluene optionally in the presence of a base. Removal of the solvent, for example by evaporation, yields the initial crude product, which will generally be the desired compound as free or its salt depending on whether the reaction is carried out in the presence or absence of a base. The free basic product may be purified by crystallisation or chromatography; or a salt may be purified by crystallisation. If desired a salt may be converted into the free base by neutralisation and if desired the free base may be salified in conventional manner.

It will be realised that, in a compound of the formula (I), interconversion of suitable substituents R[1], R[2] or R[3] may be carried out by conventional methods after formation of a compound of the formula (I). By way of example an acetamido group may be converted to an amino group an alkoxyl or acetoxyl group may be converted to a hydroxyl group, a nitro group may be reduced to an amino group, by conventional methods. Accordingly it will be realised that compounds of the formula (I) containing the substituent R[1], R[2] or R[3] which is convertible to another R[1], R[2] or R[3] group respectively are useful intermediates and as such form as important aspect of the invention.

It will also be realised that salts of the compounds of the formula (I) which are not pharmaceutically acceptable may be useful as intermediates in the preparation of pharmaceutically acceptable salts of compounds of the formula (I) or the compounds of the formula (I) themselves, and as such form an aspect of the present invention.

When $NR_2$ in the compounds of the formula (I) is substituted by two methyl groups, these may be mutually cis or trans about the $NR_2$ ring. A mixture of cis and trans isomers of the compound of the formula (I) may be synthesised non stereospecifically and the desired isomer separated conventionally therefrom, e.g. by chromatography; or alternatively the cis or trans isomer may if desired be synthesised from the corresponding cis or trans form of the compound of the formula (VI).

Cis- and trans- forms of the compound of the formula (VI) are either known as separate forms or may be separated conventionally e.g. by chromatography.

Racemates of compounds of the formula (I) wherein $NR_2$ is substituted by one or two methyl groups may be resolved conventionally, e.g. by salification with a chiral acid and separation of the resultant salts.

The following Examples illustrate the invention.

EXAMPLE I

1-[2-(4-Acetylaminobenzenesulphonamido)ethyl]-pyrrolidinium chloride (1)

4-Acetylaminobenzenesulphonylchloride (21.9 g) was added in portions to a solution of 1-(2-aminoethyl)-pyrrolidine (10.7 g, 0.9 mol) in water (250 ml). The mixture was stirred for 9 hours at room temperature. At the end of the reaction, the solution has pH 6–7. A portion of the mixture (165 ml) was removed and adjusted to pH 9.5. The precipitate from the mixture (4.9 g) was removed under suction and dissolved in ethyl acetate (170 ml). The solution was filtered and HCl gas was passed through. Precipitated chloride was isolated and recrystallised from absolute ethanol (350 ml) to give the product (27.2 g).

M.P. 220° C. yield=78% of theoretical
$C_{14}H_{21}N_3O_3S$ HCl, Mol. weight: 347,85

Compounds No: (2) and (5) were prepared in the same manner (see Table 1)

EXAMPLE II

1-[2-(4-Aminobenzenesulphonamido)ethyl]-pyrrolidinium chloride (3)

(A) Conc. hydrochloric acid (20 ml) was added to 160 ml of the mixture obtained in Example 1. This solution was warmed on a boiling water bath for 5 hours. Thereafter the solution was neutralised with $NaHCO_3$, filtered and adjusted to pH 10. The sulphonamide separated as an oil and was extracted with diethylether (4×100 ml) from the alkaline medium. The combined extracts were dried over $Na_2SO_4$ and the solvent was removed by distillation.

(B) The residue was dissolved in ethyl acetate and then HCl gas was passed through. Precipitated chloride was removed by suction and recrystallised from isopropanol to give the product (10.3 g).

M.P. 216° C. Yield=75% of theoretical $C_{12}H_{19}N_3O_2S$ HCl, Mol. weight: 305,84

Compound (4) was prepared analogously to step (A) above and recrystallised from water.

Compound (6) was prepared analogously to steps (A) and (B) substituting fumaric acid (essentially 1 aq.) for HCl gas.

EXAMPLE III

N-[2-(4-Acetylaminobenzenesulphonamido)ethyl]-morpholine (7)

A saturated solution of $NaHCO_3$ (50 ml) was added to N-(2-aminoethyl)morpholine (7.5 g, 0.05 mol) dissolved in chloroform (50 ml). Thereafter, 4-acetylaminobenzenesulphonylchloride (12.3 g, 0.05 mol) was added in portions with vigorous stirring. The mixture was stirred for 3 days at room temperature (pH 8.5). The chloroform layer was separated with a separating funnel and the aqueous layer was extracted with chloroform (3×100 ml). The combined chloroform extracts were dried over $Na_2SO_4$, and the chloroform was removed by evaporation.

The residue was recrystallised from the following:
1. ethyl acetate
2. ethyl acetate/diethylether (1:1)

M.P. 114,5°–115,5° C. Yield 29% of theoretical $C_{14}H_{21}N_3O_4S$ Mol. weight: 327,46

Compound No. (8) (see Table 1) was prepared analogously.

EXAMPLE IV

1-[3-(4-Methoxybenzenesulphonamido)propyl]-pyrrolidinium chloride (11)

4-Methoxybenzenesulphonylchloride (8.26 g, 0.04 mol) was added in portions with stirring to a solution of 1-(3-aminopropyl)-pyrrolidine (5.13 g, 0.04 mol) in 10% NaOH (100 ml), and the resulting mixture was stirred at room temperature for the next 24 hours. Unreacted sulphonylchloride was filtered off, and the filtrate was adjusted to pH 9,8 with dilute HCl.

Oily sulphonamide, which sparated out, was extracted with diethyl ether (4×100 ml) from the alcoholic mixture. The solvent was distilled off and the residue was dissolved in ethyl acetate (200 ml). HCl gas was passed through this solution. The resulting chloride was removed by suction, washed with ethyl acetate and recrystallized from isopropanol to give the product (6.0 g).

M.P. 159° C. Yield=45% of theoretical $C_{14}H_{22}N_2O_3S$ . HCl

Compounds No. (9), (10), (13), (14), (16) to (19) and (23) and

1-[2-(4-fluorobenzenesulphonamido)ethyl]pyrrolidinium chloride (15),
1-[2-(4-iodobenzenesulphonamido)ethyl]pyrrolidinium chloride (21),
1-[3-(4-iodobenzenesulphonamido)propyl]pyrrolidinium chloride (22),
1-[2-(3-trifluoromethylbenzenesulphonamido)ethyl]-pyrrolidinium chloride,
cis- (27) and trans- (28) 2,5-dimethyl-1-[2-(3-trifluoromethylbenzenesulphonamido)ethyl]-pyrrolidinium chloride, and
2,4-dimethyl-1-[2-(3-trifluoromethylbenzenesulphonamido)ethyl]pyrrolidinium chloride (29) (cis-, trans- mixture)

were prepared analogously.

EXAMPLE V 2,4-Dimethyl-1-[3-(4-iodobenzenesulphonamido)-propyl]pyrrolidine (20)

A solution of 2,4-dimethyl-1-(3-aminopropyl)pyrrolidine (4.7 g, 0.03 mol) in benzene (20 ml) was added dropwise to a solution of 4-iodobenzenesulphonylchloride (9.1 g, 0.03 mol) benzene (80 ml). After stirring the resulting mixture for six hours at room temperature, the reaction product separated as an oil. The reaction mixture was evaporated, and the residue was dissolved in absolute alcohol (800 ml) and boiled with charcoal.

The charcoal was filtered off, and the solution was diluted with water until precipitation occurred. The reaction product was evacuated, dissolved in dilute HCl and once more boiled with charcoal and filtered. The solution was made alkaline and the resulting precipitate of (20) was removed by suction.

M.P. 123° C., Yield=27% of theoretical

Mol. weight 422,32

Compounds No. (12), (24) and (30) were prepared in the same manner.

EXAMPLE VI

1-[3-(4-Carbethoxy-benzenesulphonamido)-propyl]pyrrolidinium chloride (25) (see Table 1)

1-[3-(4-Cyanobenzenesulphonamido)propyl]pyrrolidinium chloride (9 g) was boiled with 25% caustic soda solution (50 ml) for three hours. During cooling the resulting solid mass was acidified with conc. HCl (30 ml) and warmed briefly. Repeated cooling yielded a white precipitate, which was removed by suction and dried in vacuo, to yield 1-[3-(4-carboxylbenzenesulphonamido)propyl]pyrrolidinium chloride.

Dry 1-[3-(4-carboxy-benzenesulphonamide)-propyl]-pyrrolidinium chloride (9 g), absolute alcohol (25 ml) and conc. $H_2SO_4$ (0.3 ml) were boiled under reflux for 9 hours. Thereafter, the solvent was evaporated, and the residue was dissolved in water. The aqueous solution was adjusted to pH 10 with caustic soda solution and the resulting emulsion was extracted with chloroform (3×50 ml). The combined chloroform extracts were washed with water (50 ml), dried over $Na_2SO_4$ and evaporated to dryness. The residue (8,6 g) was dissolved in ethyl acetate (150 ml), and HCl gas was passed through the solution. The resulting precipitate passed through the solution. The resulting precipitate was removed by suction and recrystallised from isopropanol.

M.P. 187° C. Yield=67% of theoretical $C_{16}H_{24}N_2O_4S$ . HCl Mol. weight: 376,90

EXAMPLE VII 2,4-Dimethyl-1-[3-(2,5-dichlorbenzenesulphonamido)-propyl]-pyrrolidine (33) (see Table 2)

2,4-Dimethyl-1-(3-aminopropyl) pyrrolidine in (4.7 g, 0.03 mol) benzene (30 ml) was added dropwise at room temperature to a solution of 2,5-dichlorobenzenesulphonylchloride (7.3 g, 0.03 ml) in benzene (100 ml). Thereafter, the mixture was stirred for 4 days at room temperature until the reaction was complete. Finally, the reaction product was obtained as a viscous, oily paste. The benzene mother liquor was decanted. The residue was dissolved in water, the solution was adjusted to pH 9.8 with 10% NaOH and extractes with petroleum ether (40°–60°) (4×100 ml). The combined extracts were dried over $Na_2SO_4$ and evaporated. The residue (5 g) was recrystallised twice from 100 ml petroleum ether to yield the product (3.7 g as white needles), m.p. 65°–67° C. Yield=67% of theoretical

EXAMPLE VIII 2,4-Dimethyl-1-[3-(2,4,5-trichlorobenzene-sulphonamido)propyl]-pyrrolidinium chloride (38)

Whilst stirring, a solution of 2,4-dimethyl-1-(3-aminopropyl)-pyrrolidine (4.67 g, 0.03 mol)benzene (20 ml) was added dropwise to a solution of 2,4,5-trichlorobenzenesulphonylchloride (8.4 g, 0.03 mol) benzene (80 ml). The reaction mixture was stirred for a further eight hours at room temperature, whereby the reaction product (38) crystallised from the mixture. The precipitate was removed by suction and washed with benzene on the suction filter. The crude chloride was recrystallised from isopropanol (100 ml) to obtain the product (8.7 g).

M.p. 114°–116° C., Mol. Wt. 436,22 $C_{15}H_{21}N_2O_2SCl_3$. HCl

Yield=67% of theoretical

Compounds No. (32), (35), (37), (39), (40), (43), (45), (46), (50) and (53) and 4-methyl-1-[3-(2,3,4-trichlorobenzenesulphonamido)-propyl]-1,4-diazoniacyclohexane dichloride (36) 3,5-dimethyl-1-[2-(2,4,6-trimethylbenzenesulphonamido)ethyl]piperidinium chloride (54) were prepared analogously.

Compound (51) was prepared substantially analogously, but the chloride was neutralised and the resultant free base treated with fumaric acid to give the fumarate (51).

EXAMPLE IX 2,4-Dimethyl-1-[3-(2,3,4-trichlorobenzene sulphonamido)propyl]-pyrrolidine (34) (see Table 2)

A solution of 2,4-dimethyl-1-(3-amino-propyl) pyrrolidine (9.3 g, 0.06 mol) benzene (50 ml) was added dropwise, whilst stirring, to a solution of 2,3,4-trichlorobenzenesulphonylchloride (17.6 g, 0.06 mol) benzene (200 ml). The mixture was stirred for a further 5 hours at room temperature, whereby the reaction mixture was evaporated to dryness and the residue was dissolved in water (250 ml). The aqueous solution was extracted with diethyl ether (2×50 ml) to remove unreacted sulphochloride. The aqueous solution was then adjusted with caustic soda solution to pH 9,8 and the alcoholic solution was extracted with diethyl ether (2×100 ml). The combined extracts were dried over $Na_2SO_4$, and the solvent was distilled off. The residue was recrystallised from isopropanol (100 ml). The product (34) (9 g) was obtained. The filtrate was diluted with the same quantity of water to obtain a further 6,2 g of (34).

M.p. 73°–75° C., Mol. Wt. 399.76 $C_{15}H_{21}N_3O_2SCl_3$

Yield=61% of theoretical

Compound (41) (see Table 2) was prepared analogously.

EXAMPLE X 2,4-Dimethyl-1-(2-$\beta$-tetrahydronaphthalene sulphonamido) ethyl-pyrrolidinium chloride (56) (see Table 3)

Whilst stirring, a solution of 2,4-dimethyl-1-(3-aminoethyl)-pyrrolidine (7.2 g, 0.05 mol) in benzene (20 ml) was added dropwise to a solution of $\beta$-tetrahydronaphthalene sulphochloride (11.5 g, 0.05 mol) in benzene (80 ml). The reaction mixture was stirred for a further eight hours at room temperature, whereby the reaction product was recrystallized from the mixture as hydrochloride. The precipitate was removed by suction and washed with benzene on the suction filter. Crude hydrochloride was recrystallized from isopropanol (100 ml) to obtain the product (9.2 g).

M.p. 132°–134° C., Mol.Wt. 372.95 $C_{18}H_{28}N_2O_2S$ . HCl

Yield=49.4% of theoretical

Compounds (42), (43), (45) to (47) (see Table 2) and (57) (see Table 3), and 2,6-dimethyl-1-[2-(3-trifluoromethylbenzenesulphonamido)ethyl]piperidinium chloride (31) and 1-[3-(2,4,6-trimethylbenzenesulphonamido)propyl]pyrrolidinium chloride (44) (see Table 2)

were prepared analogously.

EXAMPLE XI

Cis-(27) and trans-(28) 2,5-dimethyl-1-[2-(3-trifluoromethylbenzenesulphonamido)ethyl]pyrrolidinium chloride 2,5-dimethyl-1-(2-aminoethyl)-pyrrolidine (8.4 g, 0.05 mol) in toluene (20 ml) was added dropwise at room temperature to a solution of 3-trifluoromethylbenzenesulphomylchloride in toluene (180 ml). Thereafter the mixture was stirred for 6 hours. Finally the mixture was stirred with $Na_2CO_3$ solution (6.15 g in 100 ml water). The toluene layer was separated off and dried over $Na_2SO_4$, and the solvent was removed by distillation. The residue (15 g) was purified and separated into its isomeric components on silica gel (14 g) by elution with chloroform/methanol/conc ammonia (190:9:1)

fraction I 4.4 1—3-trifluoromethylbenzenesulphomylchloride
fraction II 550 ml—product A
fraction III 500 ml—mixture
fraction IV 2500 ml—product B Fraction II: the solvent was removed by distillation and the residue (11 g) was dissolved in ethyl acetate (20 ml). HCl gas was passed through this solution. On cooling, the chloride crystallized out and was removed by suction. Yield 5.2 g (23% of theoretical) Mp 135° C.

Fraction IV: the solvent was removed by distillation and the residue (1.5 g) was dissolved in ethyl acetate, HCl gas was passed through this solution. The precipitate was removed by suction and recrystalized from isopropanol (30 ml). The chloride obtained (1.6 g, 10% of theoretical) had Mp 138° C.

Product A Mp 135° C. $C_{15}H_{21}N_2O_2SF_3$
  NMR: 1.41 ppm (6H, d: J6,5 Hz, 2$CH_3$) cis-isomer (27)
Product B Mp 178° C. $C_{15}H_{21}N_2O_2SF_3$.HCl NMR: 1.15 ppm 13H, d: J7 Hz, CH₃) trans-isomer (28) 1.34 ppm (3H, d: J6.5 Hz, CH₃) Cis- (55) and trans- (54) 3,5-dimethyl-1-[2-(2,4,6-trimethylbenzenesulphonamido)ethyl]piperidinium chloride were prepared and separated in an analogues manner.

Product A Mp 175° C. $C_{19}H_{26}N_2O_2S \cdot HCl$
  NMR:  9.85 ppm (3H, d: J 5.5 Hz, CH₃)   trans-isomer (54)
        1.18 ppm (3H, d: J 7.5 Hz, CH₃)
Product B Mp 235° C. $C_{19}H_{26}N_2O_2S \cdot HCl$
  NMR:  9.89 ppm (6H, d: J 5.5 Hz, 2CH₃)  cis-isomer (55)

EXAMPLE XII

1-[3-(2,4,6-trimethylbenzenesulphonamido)-propyl]-2-methylpiperidinium chloride (48)

1-(3-aminopropyl)-2-methyl-piperidine (8.02 g, 0.05 mol) in benzene (50 ml) was added dropwise at room temperature to a solution of 2,4,6-trimethylbenzenesulphochloride (11.05 g, 0.05 mol) in benzene (150 ml). Thereafter, the mixture was stirred for 8 hours, whereby the chloride reaction product precipitated from the mixture. The precipitate was removed by suction and washed with benzene on the suction filter. The crude chloride (18.2 g) was dissolved in water (100 ml). The aqueous solution was then adjusted with caustic soda solution to pH 9 and extracted with chloroform (2×100 ml). The combined extracts were dried over Na₂SO₄, and solvent was removed by distillation. The residue was dissolved in ethyl acetate (150 ml) and HCl gas was passed through this solution. The ethyl acetate was temoved by distillation and the residue was dissolved in hot isopropanol. After cooling to −6° C. crystallized chloride and was removed by suction.

Yield 9.7 g (5.1% of theoretical) Mp 153° C. $C_{18}H_{30}N_2O_2S \cdot HCl$

Compounds (49), 52 and 53 were prepared in the same manner (see Table 2).

DESCRIPTION 1

Pharmacology of Compounds

Test Procedure to Demonstrate Antiarrythmic Effects Electrostimulation Test

According to the method of SZEKERES, L. and PAPP, G. J., (Naunyn-Schmiedebergs Arch. exp. Path. Pharmak. 245, 70 (1963), arrhythmias are induced in Guinea pigs by electostimulation of the right ventricle of the heart. The animals are anesthetized with Urethane (1.2 g/kg i.p.) and artifically respired before a needle electrode is inserted in the right ventricle of the heart. Substances are given intraduodenally 30 min before the stimulation. The voltage needed for induction of extrasystoles in control animals (n=6) is compared with that required for induction of arrhythmias in treated animals (n=6). The difference is statistically evaluated by the unpaired t-test (STUDENT).

This method was used to evaluate the compounds present invention. The results are shown in following Tables 1 to 3.

TABLE 1

$$A-(CH_2)_n-NHSO_2-\underset{R_2}{\overset{R_1}{\text{C}_6H_3}}$$

| No. | A | n | R₁ | R₂ | Salt | Mp °C. | Yield % of theory | % increase of voltage electro stimulation test dose 32 mg/kg i.d. (GP; n = 6) |
|---|---|---|---|---|---|---|---|---|
| 1 | pyrrolidin-N- | 2 | N | NHCOCH₃ | HCl | 220 EtOH | 22 | 21.4* |
| 2 | pyrrolidin-N- | 3 | H | NHCOCH₃ | HCl | 183 EtOH | 28 | 14.3 |
| 3 | pyrrolidin-N- | 2 | H | NH₂ | HCl | 216 IPA | 23 | 36.2* |
| 4 | pyrrolidin-N- | 3 | H | NH₂ | — | 127 H₂O | 28 | 24.1* |

TABLE 1-continued $$A-(CH_2)_n-NHSO_2-\text{aryl}(R_1, R_2)$$

| No. | A | n | $R_1$ | $R_2$ | Salt | Mp °C. | Yield % of theory | % increase of voltage electro stimulation test dose 32 mg/kg i.d. (GP; n = 6) |
|---|---|---|---|---|---|---|---|---|
| 5 | 2,4-dimethylpyrrolidin-1-yl | 2 | H | NHCOCH$_3$ | HCl | 188.5 | 24.3 | 7.0 |
| 6 | 2,4-dimethylpyrrolidin-1-yl | 2 | H | NH$_2$ | C$_4$H$_4$O$_4$ | 157–158 | 45.6 | 15.7 |
| 7 | morpholin-4-yl | 2 | H | NHCOCH$_3$ | — | 114.5–115 | 29.1 | 43.3* |
| 8 | morpholin-4-yl | 3 | H | NHCOCH$_3$ | — | 97 | 63 | 14.3* |
| 9 | pyrrolidin-1-yl | 3 | H | CH$_3$ | HCl | 171 IPA | 20 | 22.5* |
| 10 | pyrrolidin-1-yl | 2 | H | OCH$_3$ | HCl | 118 IPA | 24 | 10.0* |
| 11 | pyrrolidin-1-yl | 3 | H | OCH$_3$ | HCl | 159 IPA | 45 | 22.5* |
| 12 | 2,6-dimethylpiperidin-1-yl | 3 | H | OCH$_3$ | HCl | 197 IPA | 56 | 2.3 |
| 13 | piperidin-1-yl | 2 | H | OCH$_3$ | HCl | 186 IPA | 34 | 4.6 |
| 14 | piperidin-1-yl | 3 | H | OCH$_3$ | HCl | 172 IPA | 61 | 11.7 |

TABLE 1-continued $$A-(CH_2)_n-NHSO_2-\text{(phenyl with } R_1, R_2\text{)}$$

| No. | A | n | $R_1$ | $R_2$ | Salt | Mp °C. | Yield % of theory | % increase of voltage electro stimulation test dose 32 mg/kg i.d. (GP; n = 6) |
|---|---|---|---|---|---|---|---|---|
| 15 | pyrrolidine-N— | 2 | H | F | HCl | 125 IPA | 37 | 24.8* |
| 16 | 2,4-dimethylpyrrolidine-N— | 2 | H | Cl | HCl | 136 EtOH | 48.5 | 9.1 |
| 17 | pyrrolidine-N— | 2 | H | Cl | HCl | 161 IPA | 34 | 21.5* |
| 18 | pyrrolidine-N— | 3 | H | Cl | HCl | 210 IPA | 34 | 19.6 |
| 19 | 2,4-dimethylpyrrolidine-N— | 2 | H | Br | HCl | 140–142 IPA | 57 | 19.8* |
| 20 | 2,4-dimethylpyrrolidine-N— | 3 | H | I | — | 123 H$_2$O | 26 | 11.8* |
| 21 | pyrrolidine-N— | 2 | H | I | HCl | 175 IPA | 30 | 30.9* |
| 22 | pyrrolidine-N— | 3 | H | I | HCl | 212 IPA | 45 | 30.9* |
| 23 | piperidine-N— | 3 | H | I | HCl | 204 IPA | 38 | 19.7 |
| 24 | pyrrolidine-N— | 3 | H | SCH$_3$ | HCl | 166 IPA | 79 | 12.9* |

TABLE 1-continued $$A-(CH_2)_n-NHSO_2-\underset{R_2}{\overset{R_1}{\text{C}_6H_3}}$$

| No. | A | n | $R_1$ | $R_2$ | Salt | Mp °C. | Yield % of theory | % increase of voltage electro stimulation test dose 32 mg/kg i.d. (GP; n = 6) |
|---|---|---|---|---|---|---|---|---|
| 25 | pyrrolidin-1-yl | 3 | H | $-\underset{\text{O}}{\overset{\text{O}}{\text{C}}}-OC_2H_5$ | HCl | 183 IPA | 67 | 16.92* |
| 26 | pyrrolidin-1-yl | 2 | $CF_3$ | H | HCl | 153 IPA | 46 | 38.0* |
| 27 | cis-2,5-dimethylpyrrolidin-1-yl | 2 | $CF_3$ | H | HCl | 135 IPA | 23 | 60.2* |
| 28 | trans-2,5-dimethylpyrrolidin-1-yl | 2 | $CF_3$ | H | HCl | 178 | 10 | 37.3* |
| 29 | 2,4-dimethylpyrrolidin-1-yl | 2 | $CF_3$ | H | HCl | 124 EtOH | 46 | 50.0* |
| 30 | morpholin-4-yl | 2 | $CF_3$ | H | HCl | 219 | 47.3 | 1.3 |
| 31 | 2,6-dimethylpiperidin-1-yl | 2 | $CF_3$ | H | HCl | 129 EE/PE | 51 | 31.8* |

TABLE 2

$$A-(CH_2)_n-NHSO_2-\text{phenyl}(R_1, R_2, R_3, R_4, R_5)$$

| No. | A | n | $R_1$ | $R_2$ | $R_3$ | $R_4$ | $R_5$ | Salt | Mp °C. | Yield % | % increase of voltage electro stimulation test dose 32 mg/kg i.d. |
|---|---|---|---|---|---|---|---|---|---|---|---|
| 32 | pyrrolidinyl | 3 | Cl | H | H | Cl | H | HCl | 203 IPA | 33.9 | 7.5* |
| 33 | 2,4-dimethylpyrrolidinyl | 3 | Cl | H | H | Cl | H | — | 65–67 PA | 67 | 3.7 |
| 34 | 2,4-dimethylpyrrolidinyl | 3 | Cl | Cl | Cl | H | H | — | 73–75 IPA | 61 | 18.75* |
| 35 | 2-methylpiperidinyl | 3 | Cl | Cl | Cl | H | H | HCl | 98 IPA | 65.5 | 1.6 |
| 36 | 4-methylpiperazinyl | 3 | Cl | Cl | Cl | H | H | 2HCl | >280 | 71 | 25.8* |
| 37 | 2,4-dimethylpyrrolidinyl | 2 | Cl | H | Cl | Cl | H | HCl | 191 | 68 | 14.8* |
| 38 | 2,4-dimethylpyrrolidinyl | 3 | Cl | H | Cl | Cl | H | HCl | 114 IPA | 66.5 | 28.9* |
| 39 | morpholinyl | 2 | Cl | H | Cl | Cl | H | HCl | 128.5–130 EtOH | 52.6 | 11.3* |
| 40 | pyrrolidinyl | 3 | Cl | H | Cl | Cl | H | HCl | 195–197 EtOH | 50 | 13.9 |

TABLE 2-continued $$A-(CH_2)_n-NHSO_2-\text{[benzene with } R_1, R_2, R_3, R_4, R_5\text{]}$$

| No. | A | n | $R_1$ | $R_2$ | $R_3$ | $R_4$ | $R_5$ | Salt | Mp °C. | Yield % | % increase of voltage electro stimulation test dose 32 mg/kg i.d. |
|---|---|---|---|---|---|---|---|---|---|---|---|
| 41 | morpholino (O-N—) | 3 | Cl | H | Cl | Cl | H | — | 145 IPA | 55 | 10.6 |
| 42 | 2-methylpiperidino | 3 | Cl | H | Cl | Cl | H | HCl | 161 IPA | 63 | 20.0* |
| 43 | 4-methylpiperazino (CH₃—N N—) | 3 | Cl | H | Cl | Cl | H | HCl | 291 EtOH | 42 | 4.1 |
| 44 | pyrrolidino | 3 | CH₃ | H | CH₃ | H | CH₃ | HCl | 201 IPA | 74.5 | 24.8* |
| 45 | 2,4-dimethylpyrrolidino | 2 | CH₃ | H | CH₃ | H | CH₃ | HCl | 153–154 IPA | 62.9 | 2.3 |
| 46 | 2,4-dimethylpyrrolidino | 3 | i-pr | H | i-pr | H | i-pr | HCl | 217–219 IPA | 70.1 |  |
| 47 | 2,6-dimethylpiperidino | 3 | i-pr | H | i-pr | H | i-pr | HCl | 224–225 H₂O | 43.5 | 17.9* |
| 48 | 2-methylpiperidino | 3 | CH₃ | H | CH₃ | H | CH₃ | HCl | 153 IPA | 57.1 | 6.0* |
| 49 | 4-methylpiperazino (CH₃—N N—) | 3 | CH₃ | H | CH₃ | H | CH₃ | 2HCl | 264 IPA | 42.7 | 7.5* |

TABLE 2-continued $$A-(CH_2)_n-NHSO_2-\text{[phenyl with }R_1, R_2, R_3, R_4, R_5\text{]}$$

| No. | A | n | $R_1$ | $R_2$ | $R_3$ | $R_4$ | $R_5$ | Salt | Mp °C. | Yield % | % increase of voltage electro stimulation test dose 32 mg/kg i.d. |
|---|---|---|---|---|---|---|---|---|---|---|---|
| 50 | pyrrolidin-N-yl | 2 | $CH_3$ | H | $CH_3$ | H | $CH_3$ | HCl | 176–177 EtOH | 64.6 | 10.6* |
| 51 | pyrrolidin-N-yl | 2 | i-pr | H | i-pr | H | i-pr | $C_4H_4O_4$ | 244–245 EtOH | 42.16 | 1.5 |
| 52 | morpholin-N-yl | 3 | $CH_3$ | H | $CH_3$ | H | $CH_3$ | HCl | 191–192 EtOH | 52.5 | 1.15 |
| 53 | 2,6-dimethylpiperidin-N-yl | 2 | $CH_3$ | H | $CH_3$ | H | $CH_3$ | HCl | 193 IPA | 59 | 16.7* |
| 54 | trans-3,5-dimethylpiperidin-N-yl | 2 | $CH_3$ | H | $CH_3$ | H | $CH_3$ | HCl | 175 IPA | 20 | |
| 55 | cis-3,5-dimethylpiperidin-N-yl | 2 | $CH_3$ | H | $CH_3$ | H | $CH_3$ | HCl | 236 EtOH | 46 | |

TABLE 3

$$A-(CH_2)_n-NHSO_2-\text{Ar}(R_1, R_2, R_3, R_4)$$

| No. | A | n | $R_1$ | $R_2$ | $R_3$ | $R_4$ | Salt | Mp °C. | Yield % | % increase of voltage electro stimulation test dose 32 mg/kg i.d. |
|-----|---|---|-------|-------|-------|-------|------|--------|---------|------|
| 56 | 2,4-dimethylpyrrolidino (CH₃, CH₃) | 2 | -CH₂CH₂CH₂CH₂- (fused ring) | | H | H | HCl | 132-134 IPA | 49.4 | 7.46 |
| 57 | morpholino (O, N-) | 2 | -CH₂CH₂CH₂CH₂- (fused ring) | | H | H | HCl | 208-210 | 56.5 | 7.8 |

Toxicity

No toxic effects were observed at the test dosages.

I claim:

1. A compound selected from the group consisting of sulfonamide of the formula:

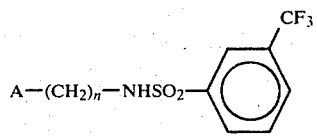

and the pharmaceutically acceptable salts thereof wherein

A is a cyclic amino radical selected from the group consisting of pyrrolidino, 2,4-dimethylpyrrolidino, 2,5-dimethylpyrrolidino, 2,4-dimethylpiperidino and 4-methylpiperazine; and n has a value of 2 or 3.

2. A compound according to claim 1 wherein n is 2 and A is pyrrolidino, 2,4-dimethylpyrrolidino or 2,5-dimethypyrrolidino.

3. A compound according to claim 1 wherein said sulfonamide is 2,4-dimethyl-1-[2-(3-trifluoromethylbenzenesulfonamido)ethyl]pyrrolidine.

4. A compound according to claim 3 wherein the conformation of the methyl groups is cis.

5. A compound according to claim 1 wherein said sulfonamide is 2,5-dimethyl-1-[2-(3-trifluoromethylbenzenesulfonamido)ethyl]pyrrolidine.

6. A compound according to claim 5 wherein the conformation of the methyl groups is cis.

7. The method of effecting an anti-arrhythmic response in humans and other animals which comprises administering thereto an effective amount of a compound according to claim 1.

8. A pharmaceutical composition comprising an amount of a compound according to claim 1 sufficient to effect an anti-arrhythmic response in combination with a pharmaceutical carrier.

* * * * *